US006312685B1

(12) United States Patent
Fisher et al.

(10) Patent No.: US 6,312,685 B1
(45) Date of Patent: Nov. 6, 2001

(54) RED BLOOD CELLS COVALENTLY BOUND WITH TWO DIFFERENT POLYETHYLENE GLYCOL DERIVATIVES

(76) Inventors: Timothy C. Fisher, 3126 El Caminito St., La Crescenta, CA (US) 91214; Jonathan K. Armstrong, 3834 Latrobe St., Los Angeles, CA (US) 90031

( * ) Notice: Subject to any disclaimer, the term of this patent is extended or adjusted under 35 U.S.C. 154(b) by 0 days.

(21) Appl. No.: 09/042,310

(22) Filed: Mar. 13, 1998

(51) Int. Cl.$^7$ .............................. A01N 63/00; A01N 1/02; C12N 5/06; C12N 5/08; C12N 11/08

(52) U.S. Cl. ...................... 424/93.7; 424/93.73; 435/2; 435/180; 435/325; 435/372

(58) Field of Search ............................. 435/2, 174, 177, 435/180, 181, 325, 372; 424/93.7, 93.73; 530/385

(56) References Cited

U.S. PATENT DOCUMENTS

| | | | |
|---|---|---|---|
| 4,179,337 | 12/1979 | Davis et al. | 435/181 |
| 5,006,333 | 4/1991 | Saifer et al. | 424/78 |
| 5,013,556 | 5/1991 | Woodle et al. | 424/450 |
| 5,214,131 | 5/1993 | Sano et al. | 530/345 |
| 5,248,766 | 9/1993 | Nelson et al. | 530/385 |
| 5,293,772 * | 3/1994 | Carr, Jr. | 73/64.41 |
| 5,386,014 | 1/1995 | Nho et al. | 530/385 |
| 5,523,492 | 6/1996 | Emanuele et al. | 568/624 |
| 5,529,914 | 6/1996 | Hubbell et al. | 435/182 |
| 5,573,934 | 11/1996 | Hubbell et al. | 435/177 |
| 5,591,669 | 1/1997 | Krimpenfort et al. | 800/2 |
| 5,605,687 * | 2/1997 | Lee | 424/78.06 |
| 5,612,034 | 3/1997 | Pouletty et al. | 424/184.1 |
| 5,643,575 | 7/1997 | Martinez et al. | 424/194.1 |
| 6,129,912 | 10/2000 | Hortin et al. | 424/93.73 |

FOREIGN PATENT DOCUMENTS

WO 95/06058  2/1995 (WO).
WO 97/28254  7/1997 (WO).

OTHER PUBLICATIONS

Abuchowski, Abraham et al., Alteration of Immunological Properties of Bovine Serum Albumin by Covalent Attachment of Polyethylene Glycol. J. Biol. Chem. 252:3578–3581, 1977.

Jeong, Seong Tae. Decreased Agglutinability of Methoxy–Polyethylene Glycol Attached Red Blood Cells: Significance as a Blood Substitute. Art. Cells, Blood Subs., and Immob. Biotech., 24(5) 503–511, 1996.

Armstrong, Jonathan K. et al. Covalent Binding of Poly-(Ethylene Glycol)(PEG) to the Surface of Red Blood Cells Inhibits Aggregation and Reduces Low Shear Blood Viscosity. Amer. Jour. of Hematology 56:26–28, 1997.

Scott, Mark D. et al. Chemical Camouflage of Antigeni Determinants: Stealth Erythrocytes. Proc. Natl. Acad. Sci. USA 94: 7566–7571, Jul. 1997.

George, Karyn Hede. Stealthy Blood Cells Manage to Survive Xenotransfusion. Jour. of NIH Research 9:26–28, 1997.

Hortin, Glen L. et al. Progress Toward Preparation of Univeral Donor Red Cells. Art. Cells, Blood Subs., and Immob. Biotech., 25(5), 487–491, 1997.

Delgado, C. et al. Coupling of PEG to Proteins by Activation with Tresyl Chloride Applications in Immunoaffinity Cell Partitioning in Separation Using Aqueous Phase Systems, Applications in Cell Biology and Biotechnology., D. Fisher and Sutherland, Eds., Plenum Press, New York, pp. 211–213, 1989.

Lenny, Leslie L Ph. D. Investigations Into Creating O Red Cells, Presentation at 51$^{st}$ American Association of Blood Banks Meeting, Philadelphia, PA, Oct. 31, 1998.

Hortin, Glen L. et al., Surface–Pegylated Red Cells as Potential Universal Donor Red Cells. Presentation at 38$^{th}$ Annual Meeting of the American Society of Hematology. 1996.

Murad, K. et al., Molecular Camouflage of antigenic determinants on intact mammalian cells: Possible applications to transfusion medicine, Presentation American Society of Hematology, 1996.

Scott, M.D., et al., Antigenic and immunogenic attenuation of erythrocytes by cell surface modification with methxy–(polyethylene glycol), Presentation American Society of Hematology, 1997.

Scott, M.D., et al., Prevention of graft–versus–host disease by chemical camouflage of leukocyte MHC class II antigens, Presentation, American Society of Hematology, 1997.

Jeong, Seong Tae, et al., The Decrease of Agglutinability of Human AB Type Red Blood Cell by Attachment of Methoxy–Polyethylene Glycol, Art. Cells, Blood Subs., and Immob. Biotech. 24(4): 358, 1996.

\* cited by examiner

*Primary Examiner*—David M. Naff
(74) *Attorney, Agent, or Firm*—Lyon & Lyon LLP

(57) ABSTRACT

Living cells are modified at their surface with specially selected polymers. Covalently attaching specially selected polyethylene glycol (PEG) derivatives to the surface of red blood cells (RBC) in aqueous media under mild conditions is a preferred example. The selected PEG derivatives dramatically reduced aggregation and low shear viscosity of RBC resuspended in autologous plasma, and inhibited RBC agglutination by blood group-specific antibodies. The morphology and deformability of the PEG-treated cells were unaltered. PEG coating of the RBC surface is applicable to the treatment of a variety of diseases characterized by vaso-occlusion or impaired blood flow, e.g., myocardial infarction, shock, and sickle cell disease. An infusion solution is prepared containing red blood cells covalently bound to a PEG derivative having a molecular weight of between 2,000 and 5,000 Daltons and a PEG derivative having a molecular weight between 10,000 and 35,000 Daltons.

10 Claims, 8 Drawing Sheets

RED BLOOD CELLS COVALENTLY BOUND WITH TWO DIFFERENT POLYETHYLENE GLYCOL DERIVATIVES

FIELD OF THE INVENTION

This invention relates to the field of modified biological cells, particularly red blood cells, specially designed polymeric agents and compositions for use therewith, and methods for the preparation and advantageous use of such cells and agents.

BACKGROUND

Red blood cells (RBC) are the oxygen delivery component of the human body and play a major role in maintaining and supporting several physiological systems that are critically important in sustaining life. Conditions that affect the health or sufficiency of the body's supply of RBC are always significant to a patient and may be life threatening.

Several characteristics of RBCs are critical. The RBCs must maintain the capability to deliver oxygen and their structural and mechanical integrity must not be compromised. Sickle cell anemia is a conspicuous example of a serious pathological condition characterized by abnormal rigidity of RBCs.

Furthermore, many diseases and medical procedures require supplementing a patient's blood supply with RBCs from a donor—typically a human source. The RBCs must be compatible with the patient. For example, the need to determine blood type and antigenicity cross-matching is a result of the requirement that RBCs must not be recognized as a foreign substance by the immune system of the patient. Where the patient's immune system attacks an infusion of RBCs, serious transfusion reactions result.

There are currently over 250 known blood group antigens, most of which are classified into 23 groups. Of these, the A, B, O, and Rh groups are of greatest significance for blood transfusion. Antibodies to A and B are naturally occurring in the majority of recipients. Rh D antigen is strongly immunogenic in Rh D negative recipients. Thus, it is universal practice to type the recipient for the A, B antigens and, except in unusual circumstances, the Rh D antigen prior to transfusion to ensure that compatible donor blood is given. The recipient's plasma is also screened to determine whether it contains alloantibodies to one or more of the minor blood group antigens on the donor RBC. The presence of an antibody which recognizes the donor cells results in the transfusion reaction mentioned above, in which the transfused RBC are rapidly destroyed. Alloantibodies develop because it is impossible to obtain a perfect match between recipient and donor with each possible combination of blood group antigens, and are most likely to develop in patients who have received multiple previous transfusions.

Still further interruptions or changes in flow characteristics of RBCs can exert profound effects on the body. Heart attacks, strokes, and other conditions accompanied by ischemia and/or reperfusion injury are among the most serious medical conditions affecting the population. The characteristics of blood flow are determined to a great degree by the viscosity of blood as it flows throughout the cardiovascular system. Viscosity is a measure of the resistance to flow and the viscosity of human blood dependent on several factors, including interactions between RBCs in blood. The higher the viscosity, the greater the force that is required to maintain a given blood flow rate.

The viscosity of human blood is highly shear-rate dependent (non-Newtonian). At high shear rates, the viscosity tends toward a minimum value, which depends upon the plasma viscosity, the volume fraction of red blood cells (hematocrit) and the deformability of each individual RBC. At high shear rates, there are no significant interactions between the RBCs. At low shear rates, the viscosity increases substantially because the RBCs aggregate together, effectively forming larger particles. This aggregation phenomenon is mediated by plasma proteins, primarily fibrinogen, but also immunoglobulins, and is completely reversible upon increasing the shear rate. The shear-rate dependence of blood viscosity leads to a disproportionate decrease in blood flow at low flow rates, such as may occur during hemorrhagic shock, or after ischemic injury to tissues. The physiological significance is that the decrease in blood flow further reduces the delivery of oxygen and nutrients to the tissues, and potentially worsens the ischemic injury.

Hemodilution is the preferred therapeutic option for reduction of blood viscosity. Hemodilution is achieved by intravenous infusion of human albumin, or a hydrocolloid polymer solution, e.g., dextran or a modified starch, such as HES (hydroxyethyl starch), as a plasma volume expander. Hemodilution has been shown to be effective in the management of acute or chronic ischemia, such as stroke, cerebral vasospasm, critical limb ischemia and peripheral vascular disease. Blood viscosity is reduced due a combination of the reduced hematocrit and dilutional effect on the plasma fibrinogen concentration. In general, the practice of hemodilution in clinical applications aims to lower the hematocrit to between 0.30 and 0.35, at which level the reduction in $O_2$ carrying capacity by the RBCs is offset by increased blood flow due to flow resistance and a consequent increase in cardiac output. However, hemodilution is not an appropriate option for disorders such as myocardial ischemia in which cardiac reserve may already be compromised, pre-existing cardiac failure, or sickle cell disease (pre-existing anemia). In such cases, an alternative means to reduce blood viscosity without significant hemodilution would be desirable.

Polyethylene glycol (PEG) is an amphiphilic linear polymer, which is non-mimmunogenic, non-toxic and chemically inert in biological systems. PEG-modified biomolecules such as albumin have been shown to be intrinsically less immunogenic and to have a prolonged circulation time in rats whose immune systems have been pre-sensitized with unmodified bovine albumin. The covalent attachment of PEG is now commonly used to modify many proteins, enzymes, drugs and artificial surfaces that come into contact with human blood. PEG-modified enzymes are in clinical use, e.g., PEG-adenosine deaminase for the treatment of severe combined immunodeficiency, and PEG-modified hemoglobins have been developed for use as hemoglobin-based oxygen carriers (HBOC) as blood substitutes. Liposomes coated with PEG have been evaluated for use both as artificial hemoglobin carriers and as drug delivery systems.

Despite these seemingly diverse applications, essentially two reasons exist for modifying a protein or biomolecule with PEG. First, a potentially antigenic protein or enzyme labelled with PEG is not susceptible to attack by the immune system. The extremely hydrophilic nature of the PEG molecule, which in aqueous solution is surrounded by a large volume of coordinated water molecules to establish a hydrodynamic radius, contributes to the reduced antigenicity of PEG-labelled biomolecules. Once the PEG molecule is attached to a biomolecule, such as a protein near to a potentially antigenic site, the PEG molecule with its associated hydration sphere sterically hinders the approach of antibodies or other immunoproteins. Second, PEG-modification alters the physical properties of the substance to which the PEG is attached. For example, in PEG-modified bovine hemoglobin, aside from reducing the potential antigenicity of the bovine protein, the PEG increases the molecular weight of the hemoglobin, which reduces extravasation and slows the clearance from the blood stream and reduces renal toxicity. In the case of PEG-modified liposomes, the PEG-coating increases the hydrophilicity of the surface, prevents aggregation (flocculation) of the particles in suspension, and significantly delays uptake by the reticuloendothelial system. PEG molecules are also covalently bound to plastic surfaces to improve biocompatibility and to solubilize pharmaceutical agents that would otherwise be too hydrophobic for use.

Therefore, the use of reactive PEG intermediates has recently been widely applied to modify synthetic surfaces, proteins, liposomes, and drugs. The PEG coating of these substances has enabled prolonged circulatory times, increased biocompatibility, and reduced immunogenicity. However, because most PEG-modification techniques require highly non-physiological conditions, the direct bonding of PEG to living cells has not been practical nor widely practiced.

Poloxamer 188 (P188), also known as Pluronic F68, is an agent that inhibits RBC aggregation and reduces blood viscosity in vitro. A pharmaceutical preparation of P188 (RheothRx® injection) has been shown to improve blood flow in ischemic tissues and to reduce myocardial infarct size in animal models. Recent clinical studies have demonstrated significant potential for RheothRx® in the treatment of myocardial infarction and sickle cell crisis.

The poloxamer molecule consists of two hydrophilic poly(ethylene glycol) (PEG) chains connected by a hydrophobic poly(propylene glycol) (PPG) core to form an A-B-A triblock copolymer of PEG(A) and PPG(B) having a total molecular weight of approximately 8400 Daltons (80% PEG and 20% PPG). The mechanism of action of P188 appears to result from adsorption of the hydrophobic PPG core onto the RBC surface, with the hydrophilic PEG segments extending outward from the cell surface, forming a steric barrier which inhibits RBC aggregation and consequently reduces low shear blood viscosity by preventing cell-cell or cell-plasma interactions. However, P188 suffers from certain drawbacks. A relatively high plasma concentration of P188 (>1 mg/ml) is needed to achieve a significant reduction of RBC aggregation. As P188 undergoes rapid renal clearance from the circulation ($t_{1/2}$=5 hr), a continuous intravenous infusion of 30–60 mg/kg/hr is required to maintain a therapeutic plasma level, which amounts to a total dose of 50 g/day or more. Therefore, P188 is somewhat inefficient (low potency) at lower concentrations and is toxic at concentrations high enough to yield significant benefits.

These disadvantages are a consequence of the very weak hydrophobic interaction between the hydrophobic PPG and the RBC, and the small size of the molecule, which causes it to be excreted very rapidly (half-life 2–5 hours). This disadvantage cannot be remedied by increasing the size or the relative proportions of PEG and PPG in the molecule—Pluronics larger than F68, e.g. F108 and F127, which have a larger hydrophobic segment and which might be expected to bind more strongly to RBC, tend to self-associate when added to blood, and thus promote, rather than inhibit, red cell aggregation.

SUMMARY OF INVENTION

Pursuant to this invention, an appropriate water-soluble polymer is either covalently bound, or otherwise bound with very high affinity, to the surface of a living biological cell, particularly a red blood cell (RBC). This invention achieves the exclusion of plasma proteins (including fibrinogen and immunoglobulins) from the cell surface, and the inhibition of cell-cell adhesive interactions. Data are presented below to demonstrate the exclusion of plasma proteins from RBCs. Data demonstrating the effect of this invention on RBC-RBC adhesive interactions leading to a very effective rheologic improvement are also presented. The therapeutic advantage of the invention is derived in part from a maximal rheologic benefit achieved with a relatively small dose of polymer, thereby reducing any toxicity problems. Moreover, the therapeutic activity of the invention is a long-lived effect—covalently bonded polymer theoretically remains effective for the lifetime of the treated RBC (up to 120 days).

The treatment enabled by this invention is more effective than P188 as an inhibitor of RBC aggregation in vitro, has the theoretical advantages that only milligram quantities of PEG are required to adequately cover the surfaces of the whole circulating RBC population, can be only minimally volume expanding (assuming exchange transfusion), and that a single treatment should be sustained for the lifetime of the RBC.

The polymer species contemplated by the invention include PEG derivatives, including, but not limited to, those for which data is provided below, and oxyethylene/oxypropylene copolymers (e.g., poloxamers-commercially known as Pluronics, e.g., F38, F68, F88, F127) and having a molecular weight of between approximately 4,000–14,000. Also, poly saccharides such as dextran and other sugars, starches such as HES, and other biocompatible polymers such as polyrinylpyrrolidone are also included within the scope of the invention.

Optimal techniques to covalently bond certain specially selected PEG derivatives onto the surface of normal, viable red blood cells (RBC) are a key component of the invention described below. When bound to the RBC surface, these PEG molecules and their associated water molecules form a coating analogous to a thin layer of hydrogel. This methodology creates a steric barrier, which prevents large molecules, such as plasma proteins, from reaching the RBC surface. However, because the barrier is comprised mostly of water, small molecules (e.g., sugars, amino acids) and dissolved gases freely diffuse through the PEG layer to substantially preserve the function and viability of the RBC.

The PEG coating of red blood cells has two significant beneficial effects. First, the RBC surface is less accessible to antibodies and the blood group antigens are masked to the immune system. Masking of the RBC blood group determinants by PEG bound to the RBC surface circumvents the basis for adverse blood transfusion reactions. Second, a PEG-modified RBC surface reduces or abolishes RBC-RBC aggregation by preventing the interaction of fibrinogen with the RBC surface, which results in a dramatic reduction in blood viscosity at low shear rates. Reduction of blood viscosity directly or indirectly contributes to the alleviation of acute or chronic ischemia by decreasing aggregation, increasing blood flow and improving oxygen delivery.

One of the methods of the present invention provides a simple means to coat RBC surfaces with PEG under mild, near-physiological conditions with no apparent adverse effects on RBC morphology or deformability. This method yielded reduced RBC aggregation and reduced blood viscosity more effectively than treatment of plasma with P188, the most potent inhibitor of RBC aggregation currently in clinical use. The formulations of this invention are applicable to the treatment of ischemic vascular disorders, notably myocardial infarction, vasoocclusive crisis in sickle cell disease, and resuscitation after hemorrhagic shock. Where a transfusion is required, the use of PEG-modified RBC would not only restore oxygen-carrying capacity, but would also reduce low shear viscosity to improve blood flow in underperfused tissues.

PEG-modification of the RBC surface also inhibits agglutination by antibodies against blood group antigens. Inhibition of antibody binding by PEG-coating of RBC prior to transfusion should prolong the survival of transfused erythrocytes in patients with existing alloantibodies, or reduce the incidence of alloimmunization in multiply-transfused patients. While increased RBC survival alone would be beneficial for various kinds of chronic anemia, the combination of reduced blood viscosity and enhanced RBC survival is especially advantageous for the treatment of patients with sickle cell disease, in whom ischemia rather than anemia is the primary cause of morbidity.

In a first embodiment of the invention, red blood cells (allogeneic or autologous) are treated ex vivo with a chemically reactive derivative of a polymer (e. g., PEG) which covalently binds to the RBC surface. This produces blood for transfusion (or re-infusion to the same patient) which has greatly reduced low-shear viscosity due to inhibition of cell-cell and cell-fibrinogen interactions. The low-viscosity blood is advantageous for transfusion in sickle cell disease, hemorrhagic or septic shock. It also would be effective for the management of acute and chronic ischemia e myocardial infarction, stroke, peripheral vascular disease. However, because transfusion is not the usual clinical practice in ischemic vascular disease, an injectable or infusible form of the polymer treatment may be more practical for general clinical use, as described below.

In another embodiment, RBCs are treated with a covalently-binding polymer to produce blood for transfusion with enhanced blood group compatibility. The polymer coating prevents antibodies (immunoglobulins) from reacting with antigenic molecules on the red cell surface, and thereby prevents the recognition by the recipient of mismatched blood group antigens on donor RBCs. The polymer coating thus protects the RBCs from destruction when transfused to a patient with existing antibodies to a blood group antigen present on the donor cells. The polymer coating also prevents interaction between blood group antigens on the donor red blood cells and cellular elements of the recipient's immune system, which reduces the extent of alloimmunization. The applications of this embodiment are: 1) to prepare "universal donor" red blood cells from allogeneic red blood cells which can be transfused to any patient without regard to blood group; 2) to prevent the development of antibodies to blood group antigens (alloimmunization) in patients who require chronic blood transfusion therapy; 3) to protect donor RBC with incompatible blood group antigens given to patients who have one or more existing antibodies to those antigens and for whom fully matched blood cannot be found; 4) to protect autologous RBC in patients with autoimmune hemolytic anemia (i.e., with antibodies to antigens on their own RBC); and 5) for use in extreme emergencies when there is insufficient time to type and crossmatch blood before transfusion.

In yet another embodiment, a suitable polymer (e., PEG or dextran) is conjugated with high-affinity ligand targeted to specific protein, glycoprotein or glycolipid structures on the RBC surface, and administered intravenously to reduce low-shear blood viscosity. The high-affinity ligand can, if desired, be designed to chemically react with the target after initial binding, to form a permanent covalent bond. Once in the circulation, the polymer binds to RBCs, thereby preventing RBC aggregation and decreasing low-shear blood viscosity. This type of rheologic therapy is appropriate for applications in myocardial infarction, stroke, peripheral vascular disease, reperfusion injury, hemorrhagic and septic shock, sickle cell disease, and disease states characterized by impaired blood flow. In general, for myocardial infarction and possibly stroke, this therapy would be used concurrently as an adjunctive therapy together with treatment aimed at reperfusing the occluded vessel, such as administration of the thrombolytic agent streptokinase or TPA, or with balloon angioplasty.

In each of the above-embodiments, the polymers and/or the living cells are in a physiologically compatible solution for intravenous infusion prepared by techniques that are well known in the art.

DESCRIPTION OF FIGURES

FIG. 1a is a monofunctional PEG-CN derivative having a molecular weight of approximately 5000 Daltons: methoxy-PEG-4,6-dichloro-s-triazine (mPEG-CN). FIG. 1b is a difunctional dichloro-s-triazine derivative of PEG (PEG-CN). Data for two different molecular weights: 3350 Daltons ($X \approx 76$) and 18500 Daltons ($X = 420$) are disclosed below.

DETAILED DESCRIPTION OF INVENTION

Figure 1A:
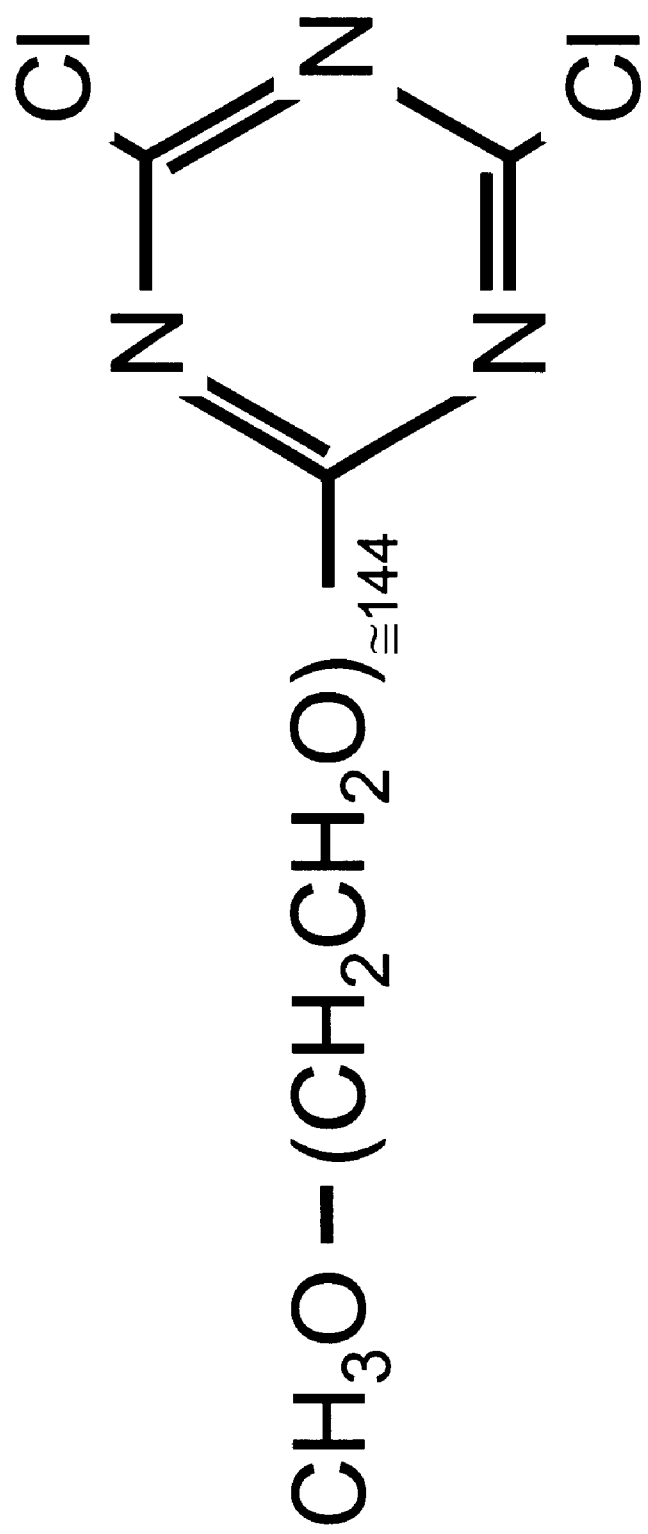
FIGS. 1a and 1b are derivatives of PEG.

The invention described herein is founded, in part, on the realization that to maximize the rheologic benefit, a specially selected polymer or combination of polymers needs to be either bound with very high affinity or covalently bound to the RBC surface. A strongly-bound surface coating of a polymer or combination of polymers selected according to the criteria described herein creates a steric barrier which prevents large plasma proteins (such as fibrinogen and immunoglobulins) from approaching the surface of the living cell. The data presented herein shows that a PEG polymer of appropriate molecular weight, or combination of PEG polymers with appropriate, but distinct, molecular weights inhibits RBC-RBC adhesive interactions, leading to a very effective reduction of low-shear blood viscosity are anti-aggregant, and are immunologically masked. However, the bound polymer presents no significant barrier to the free diffusion of small molecules such as dissolved gases (i.e., oxygen and carbon dioxide), electrolytes, sugars, amino acids and water in and out of the cell.

This invention includes a PEG-modification or coating technique that is inexpensive, rapid and simple to perform. Because the technique is designed to be compatible with physiological conditions, the technique causes no damage to the target living cell as demonstrated by the data for RBCs presented herein. This invention also includes optimal PEG-derivatives, which, together with the coating technique enable conjugation to the target cell as described below. Pursuant to this invention, one or both ends of the PEG molecule is modified by the addition of a chemically reactive functional group, which acts as a "linker" to bind the otherwise inert PEG molecule to the target. Although a wide range of different PEG derivatives have been synthesized for binding to protein, and many of these are commercially available, most of these derivatives react primarily with available amino groups (lysine residues) on the target proteins. (J. M. Harris, Poly(ethylene Glycol) Chemistry: Biotechnical and Biomedical Applications; Plenum Press, New York 1992; S. Zalipsky, Chemistry of poly(ethylene glycol) conjugates with biologically active molecules, *Adv. Drug Delivery Rev.*, 16(1995) 157–182; C. Delgado, G. E. Francis and D. Fisher, The uses and properties of PEG-linked proteins, *Crit. Rev. Ther. Drug Carrier Syst.*, 9(1992) 249–304). These existing PEG derivatives vary in terms of their reactivity and their optimal reaction conditions.

To PEG-modify RBCs without loss of viability, this invention discloses PEG derivatives that are capable of modifying living cells existing in aqueous media and under conditions as near to physiological as possible. To verify the utility of the compounds disclosed herein, twenty different monofunctional PEG derivatives, each of 5000 Daltons molecular weight, were incubated with washed RBC suspended in triethanolamine buffer at pH 8.6 for 2 hours at 25° C. The RBC were then washed and resuspended in autologous plasma. Successful PEG-coating of the cell was verified first by measuring inhibition of RBC aggregation, using an automated RBC aggregometer and by visually examining the rate and extent of rouleaux formation after a well-mixed sample was introduced into a chamber between a microscope slide and a cover slip. The results demonstrate that certain PEG-derivative formulations are particularly effective for targeting living cells.

Referring to FIG. 1a, monomethoxy poly(ethylene glycol)-4,6-dichloro-s-trizine (obtained from Sigma Chemical Co., St. Louis, Mo.) is considerably more effective than the others. PEG-dichlorotriazine derivatives react rapidly in aqueous media at alkaline pH with the amino groups of lysine residues and may also react with thiol groups. The N-hydroxy-succinimidyl derivatives, mPEG-SC and mPEG-SPA (Shearwater Polymers, Huntsville, AL), also showed a tendency to reduce RBC aggregation, but to a much lesser extent. Many other PEG derivatives tested, including PEG-aldehyde, PEG-epoxide, PEG-hydrazide, PEG-tresylate or PEG-maleic anhydride, each fail to show significant inhibition of RBC aggregation.

Figure 1B:

Referring again to FIG. 1a, this molecule is a monofunctional derivative prepared from PEG with one end capped by an unreactive methyl group (i.e., monomethoxy PEG, or mPEG). The derivative is prepared by reacting the hydroxyl-terminated end of the MPEG molecule with an excess of 2,4,6-trichloro-s-triazine in a non-aqueous solvent such as benzene (A. Abuchowski, T. van Es., N. C. Palczuk and F. F. Davis, Alteration of immunological properties of bovine serum albumin by covalent attachment of polyethylene glycol., *J. Biol. Chem.*, 252, 3578–3581, 1977; M. Bessis, R. I. Weed and P. Leblond. *Red Cell Shape*, Springer-Verlag, New York, 1973). The trivial name for trichlorotriazine ($C_3N_3Cl_3$) is cyanuric chloride; hence, this derivative is commonly abbreviated as PEG-CN. (Note that the —CN suffix denotes the heterocycle $C_3N_3$, and does not refer to cyanide (C≡N)). Studies were performed using mPEG-CN of 5000 Daltons molecular weight obtained from Sigma Chemical Co., St. Louis, Mo. Referring to FIG. 1b, two di-functional PEG-CN derivatives of 3350 and 18500 Daltons molecular weight were also synthesized according to the method of Abuchowski et al. (A. Abuchowski, T. van Es., N. C. Palczuk and F. F. Davis, Alteration of immunological properties of bovine serum albumin by covalent attachment of polyethylene glycol., *J. Biol. Chem.*, 252, 3578–3581, 1977). Using these selected PEG derivatives, the PEG coating technique was conducted using RBCs as exemplary living cells.

PEG-coating of RBC was performed by first washing the RBCs and then suspending at 50% hematocrit in 30 mM triethanolamine buffer at pH 8.3, with 0.5% human serum albumin (HSA). The desired concentration of the selected PEG-CN derivative was rapidly dissolved in a small volume of buffer and added to the RBC suspension. The RBC-polymer mixture was then rocked gently at room temperature for 30 minutes, after which the RBC was washed twice in buffer. The coated RBC were resuspended at 40% hematocrit in autologous plasma.

After PEG-coating, RBC showed normal morphology (i.e., biconcave discs) as evaluated by optical microscopy, except when very high PEG concentrations were used, which resulted in echinocytosis. RBC deformability was measured using the Cell Transit Analyzer (CTA, ABX, Montpellier, France), which measures the time taken for RBC to deform and pass through 5 micron diameter pores. The deformability of PEG-coated RBC was unchanged from control, except at high PEG concentrations and only when the morphology was also compromised. Oxygen uptake and release, measured using a Hemox-Analyzer Model B (TCS Medical Products Co., Huntingdon, Pa.) was found to be identical to control RBC.

EXAMPLE 1

Reduction of Blood Viscosity By PEG-Modified RBC

Figure 2:
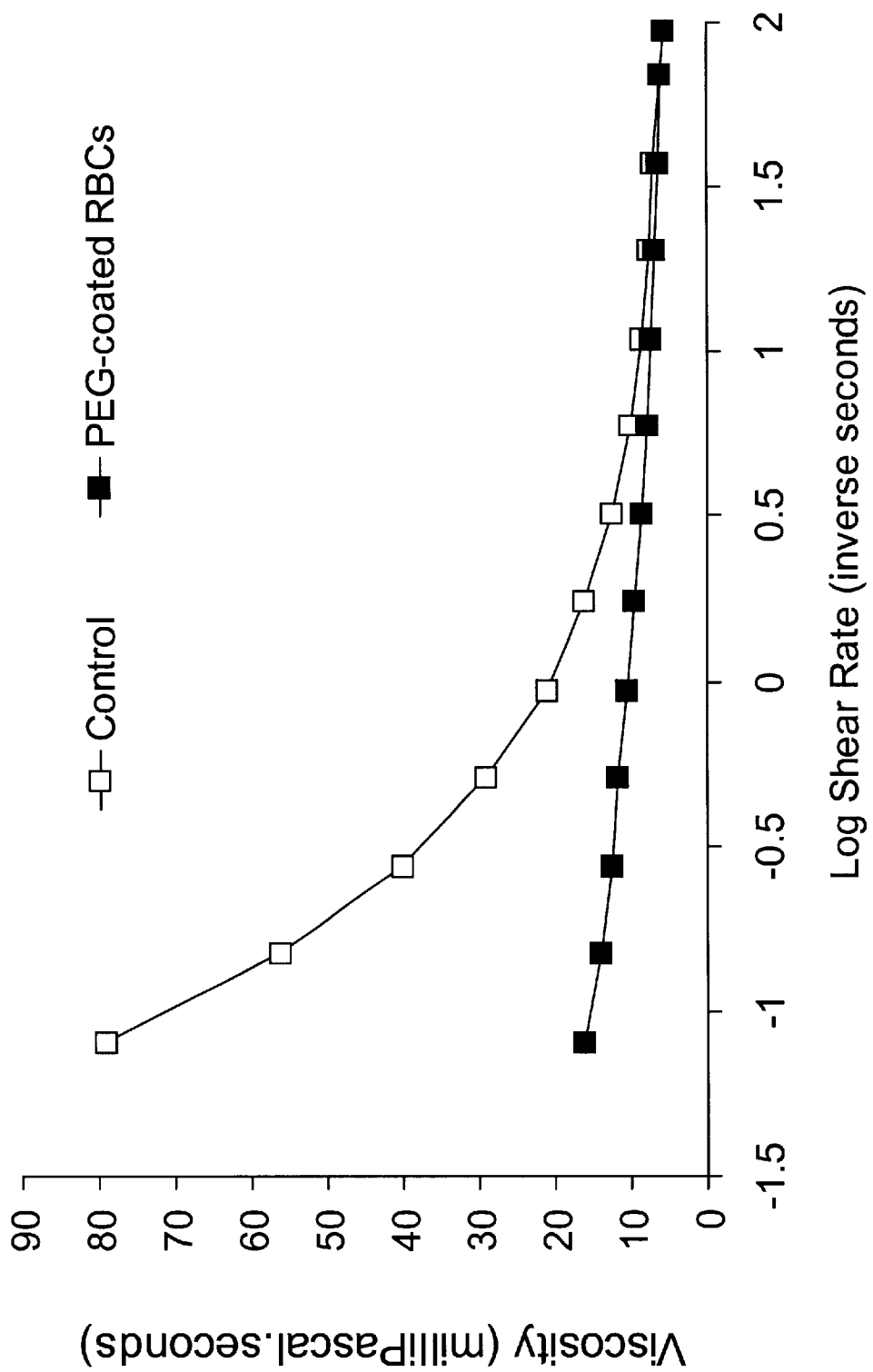
FIG. 2 shows the effect of PEG-coating on whole blood viscosity by the shear-viscosity relationship of RBC incubated with 5 mg/ml mPEG-CN 5000 and resuspended at 40% hematocrit in autologous plasma. The PEG-coated RBC (filled squares) show reduced low-shear viscosity, but no change in high shear viscosity, which is consistent with complete inhibition of RBC aggregation. The data indicate that the PEG-coated RBC show comparatively small changes in viscosity as a function of the shear rates.

Referring to FIG. 2, the effect of PEG-coating on whole blood viscosity is shown. The viscosity of control RBC and PEG-coated RBC were compared over a range of shear rates using a Couette viscometer (Contraves LS30, Contraves AG, Switzerland). The control RBC show a typical steep change in viscosity with shear rate. In contrast, the viscosity for the PEG-coated RBC (lower curve) showed very little shear dependence, i.e., the blood behaved in a nearly Newtonian manner, consistent with the complete elimination of RBC-RBC aggregation. At the higher shear rates(10–100 sec$^{-1}$), the curves for control and PEG-coated RBC exactly converged. Given that the hematocrit and plasma viscosity were identical for the two samples, this confirms that the RBC deformability was not altered by the PEG-coating. Note that the amount of bound PEG required to abolish RBC aggregation and minimize low shear viscosity is much lower than that required for antigen masking (see Example 2 below), and is therefore less likely to impair the function or compromise the survival of the RBC—an essential requirement for non-transfusion-related applications.

Figure 3:
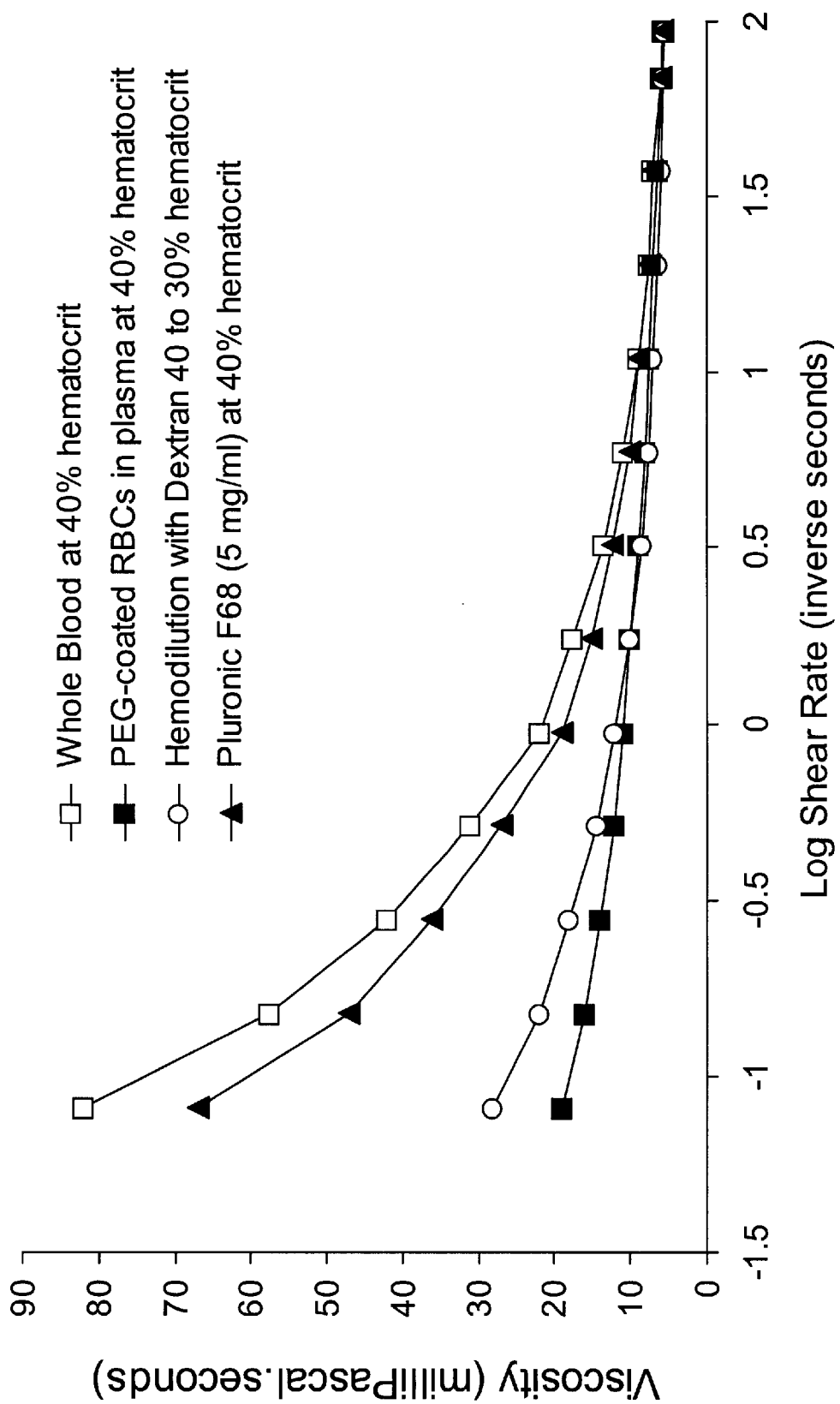
FIG. 3 measures the viscosity reduction as a function of shear rate achieved with four separate formulations: (1) whole blood (40% hematocrit), (2) whole blood hemodiluted with dextran 40 to 30% hematocrit, (3) PEG-coated red blood cells (40% hematocrit in plasma), and (4) Pluronic F68 (5 mg/ml) (40% hematocrit).

Referring to FIG. 3, the viscosity of RBC in plasma at 40% hematocrit as a function of shear rate is shown and compared with RBC hemodiluted with dextran with PEG-modified RBC, and with Poloxamer 188 (P188). The curve for untreated, control RBC demonstrates the well-established shear-dependent decrease in viscosity: At low shear the viscosity is markedly elevated due to RBC aggregation, while with each stepwise increase in shear, the viscosity decreases due to the disruption of RBC aggregates. RBC treated with mPEG-CN showed a much reduced low shear viscosity (75% less than control). By comparison, Poloxamer 188 at 5 mg/ml was less effective, reducing the low shear viscosity by approximately 30%. RBC aggregation measured by the Myrenne aggregometer (M mode) was reduced by 93±8% after mPEG-CN treatment compared to 33±9% for 5 mg/ml Poloxamer 188 (mean±sd). Microscopic examination of RBC in autologous plasma showed that >98% of RBC remained as biconcave discocytes after mPEG-CN treatment. The only observable microscopic difference between mPEG-coated and control RBC was the absence of rouleaux formation. No change in RBC deformability was detected with the Cell Transit Analyzer.

Referring again to FIG. 3, the potential of PEG-coated RBC as a rheological treatment, is demonstrated by comparing the viscosity reduction observed in vitro by either hemodilution or the addition of Poloxamer 188 (BASF, Parsippany, N.J. as compared with that for the PEG-coated RBC of this invention. As noted above, hemodilution from 40% to 30% hematocrit with dextran 40 (Sigma) resulted in a large drop in viscosity, especially low-shear viscosity. However, the low-shear viscosity reduction was still lower for the PEG-coated RBC suspension at 40% hematocrit, in 100% plasma, than for the hemodiluted blood at 30% hematocrit. Thus, the PEG-coating achieved a greater reduction in viscosity, but without compromising the oxygen-carrying capacity of the blood. In contrast, Poloxamer 188 caused only a modest reduction in low shear viscosity at a concentration of 5 mg/ml plasma, which represents the upper limit of the concentration that would be achieved in clinical use (R. C. Jewell, S. P. Khor, D. F. Kisor, K. A. K. LaCroix and W. A. Wargin, Pharmacokinetics of RheothRx injection in healthy male volunteers, *J. Phanm. Sciences*, 86(1997) 808–812).

EXAMPLE 2

Masking of Blood Group Antigens By PEG-Modification of RBC

The extent of antigen masking that could be achieved by PEG coating was examined using the PEG-CN derivatives described above, alone and in combination, over a range of concentrations. Standard blood bank serology techniques (agglutination testing) were used for the initial screening of antigen masking; blockade of antibody binding was later quantified directly by flow cytometry, Agglutination studies were conducted using a standard tube test, with antisera (Immucor Inc., Norcross, GA and Gamma Biologicals Inc., Houston, Tex.) to a selected range of antigens from the Rh and other blood groups, many of which are commonly implicated in delayed hemolytic transfusion actions. The standard glass tube was pre-coated with human serum albumin (HSA) by rinsing with APES (Sigma Chemical Co., St. Louis, Mo.), washing with water, soaking in 3% HSA in PBS for 5 min., and fmally rinsing with water and allowing to dry before use. Table 1 compares the direct agglutination observed for control (untreated) RBC and RBC incubated with PEG-CN 18500 Daltons at 20 mg/ml. The striking result was that direct agglutination, which was 3± or 4± for the control RBC, could be completely blocked by the PEG-CN 18500 for each of the antisera tested.

TABLE 1: Direct agglutination tests, using antisera for several clinically important blood group antigens, for control (untreated) RBC and RBC incubated with PEG-CN 18500 at 20 mg/ml

|  | Rh Antigens |  |  |  |  | Other Blood Group Antigens |  |  |  |  |  |
| --- | --- | --- | --- | --- | --- | --- | --- | --- | --- | --- | --- |
|  | D | c | C | e | E | Le$^b$ | Jk$^a$ | Jk$^b$ | Fy$^a$ | N | P$_1$ |
| Control | 4+ | 4+ | 4+ | 4+ | 4+ | 3+ | 4+ | 4+ | 3+ | 3+ | 3+ |
| PEGRBC | 0 | 0 | 0 | 0 | 0 | 0 | 0 | 0 | 0 | 0 | 0 |

The other PEG derivatives, mPEG-CN 5000 and PEG-CN 3350, also inhibited agglutination, but were slightly less effective, typically giving a 1+ reaction.

In contrast, it proved more difficult to block agglutination by antisera to the A and B antigens. With each of the PEG derivatives, agglutination was observed with the full-strength antisera. Thus, it was necessary to prepare serial dilutions of the anti-A and anti-B reagents to compare the titers at which agglutination was prevented. TABLE 2: Titers (reciprocal dilutions) at which anti-A antisera no longer caused detectable RBC agglutination, for RBC coated with three different molecular weights of PEG. A high titer indicates strong reactivity. Masking of the A antigen by PEG-coating is indicated by a reduction in titer.

|  | anti-A titer | | |
| --- | --- | --- | --- |
| Concentration (mg/ml) | PEG 18500 | PEG 3350 | mPEG 5000 |
| 0 | 512 | 512 | 128 |
| 10 | 16 | 128 | 64 |
| 20 | 4 | 64 | 32 |
| 30 | 2 | 64 | 16 |
| 40 |  | 16 | 16 |

Again, the PEG 18500 proved to be the most effective; the minimum titer at which detectable agglutination was observed decreased from 512 to 2 with 30 mg/ml PEG-CN 18500. Smaller PEGs were less effective; the titer was reduced to 16 at 40 mg/ml for both PEG-CN 3350 and mPEG-CN 5000. Higher concentrations of PEG were not tried, because between 30 and 40 mg/ml the normal RBC morphology was lost, and all cells became spheroechinocytic when examined in autologous plasma.

Because the prevention of agglutination does not necessarily indicate that the RBC are "antigenically silent," the blocking of antibody binding by techniques other than agglutination must be demonstrated. Thus, flow cytometry was used to precisely quantitate the degree of blockade of antibody binding.

An FITC-conjugated goat anti-human $I_gG$ antibody (Sigma) was used to quantitate the amount of anti-D antibody bound to RBC after incubation with increasing concentrations of PEG-CN 3350 and PEG-CN 18500. The control and treated RBC were incubated with the primary anti-D antibody at a high antibody-to-cell ratio to prevent direct agglutination, washed 4 times, and then incubated with the FITC-conjugated secondary antibody, again at a high antibody-to-cell ratio. The cells were then analyzed by flow cytometry. Even with the above precautions, some agglutinates were observed for the control (non-PEG-coated) RBC, though these were typically less than 50% of the total number of events. Thus, for analysis, a gate was set using the forward and side scatter pattern to include only single RBC, and exclude agglutinates of 2 or more cells.

Figure 4:
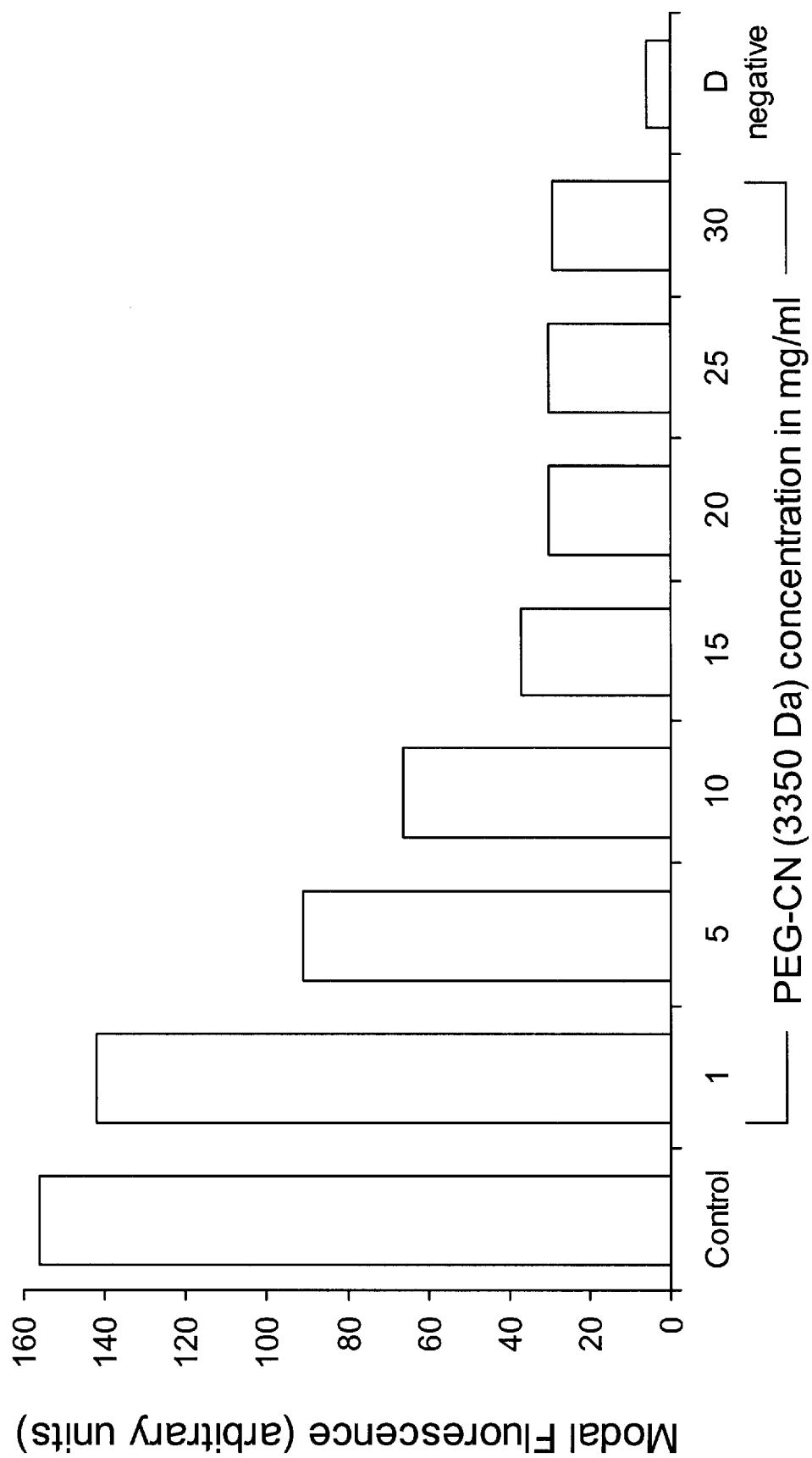
FIG. 4 shows the effect of coating with PEG 3350 on anti-D antibody binding measured by flow cytometry using FITC-labelled anti-human IgG showing the modal fluorescence of D+ control RBC as a function of increasing PEG-CN 3350 concentration.

Referring to FIG. 4, the effect of coating with PEG 3350 on anti-D binding is shown. The first column shows the modal fluorescence (in arbitrary units) of D positive (control) RBC. The last column shows the background fluorescence of D negative RBC. A progressive decrease in antibody binding was observed with increasing PEG concentration, which reached a minimum of about 85% inhibition at a PEG-CN 3350 concentration of 20 mg/ml. No additional effect was observed at higher PEG concentrations.

Figure 5:
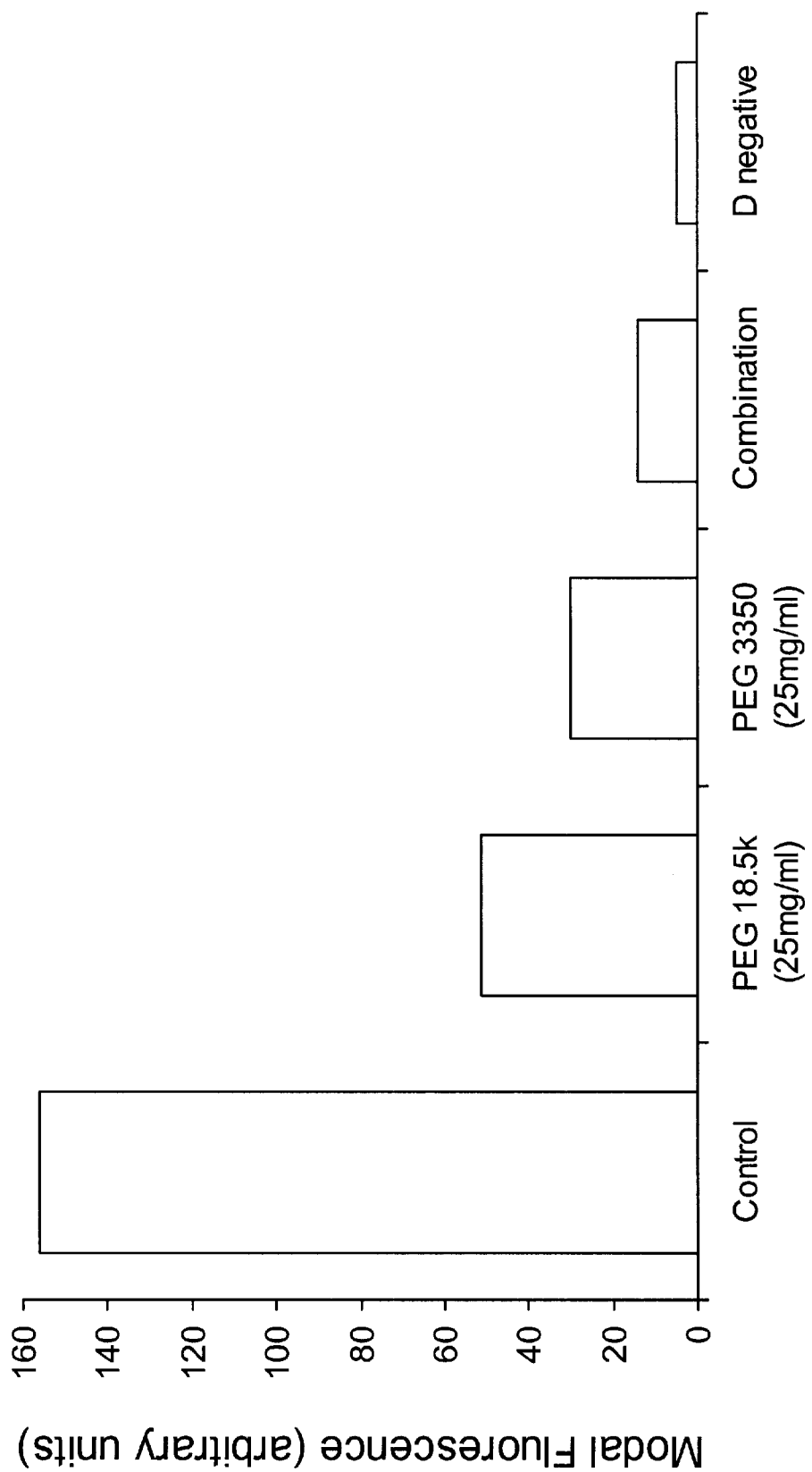
FIG. 5 shows the effect of anti-D antibody binding to red blood cells measured by flow cytometry using FITC-labelled anti-human IgG after incubation with PEG-CN 3350 and PEG-CN 18500 and a 50/50 combination of the two concentrations.
Figure 6:
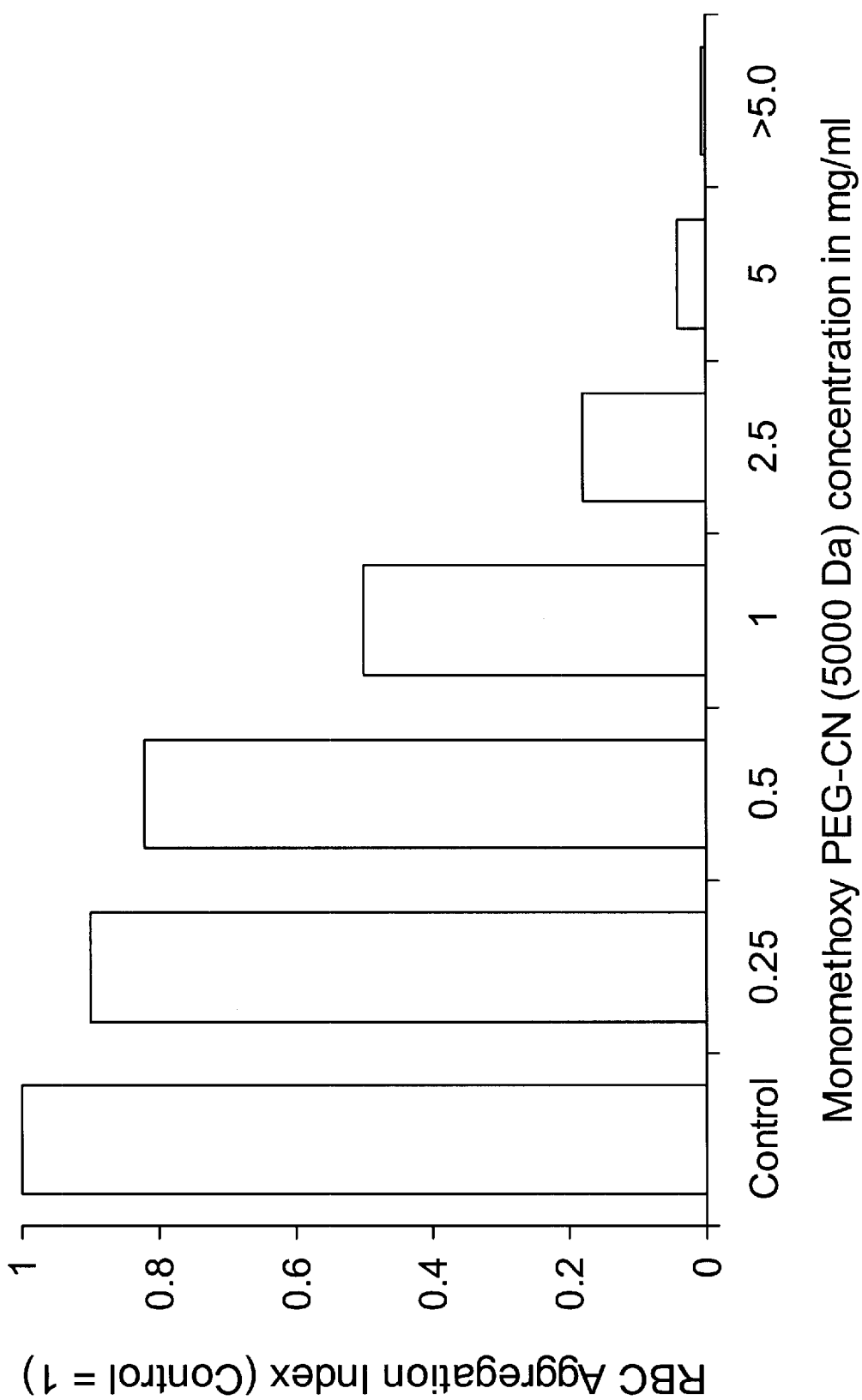
FIG. 6 is a measurement of the red blood cell aggregation as a function of increasing concentration of mPEG-CN 5000 relative to control (untreated) RBC.
Figure 7:
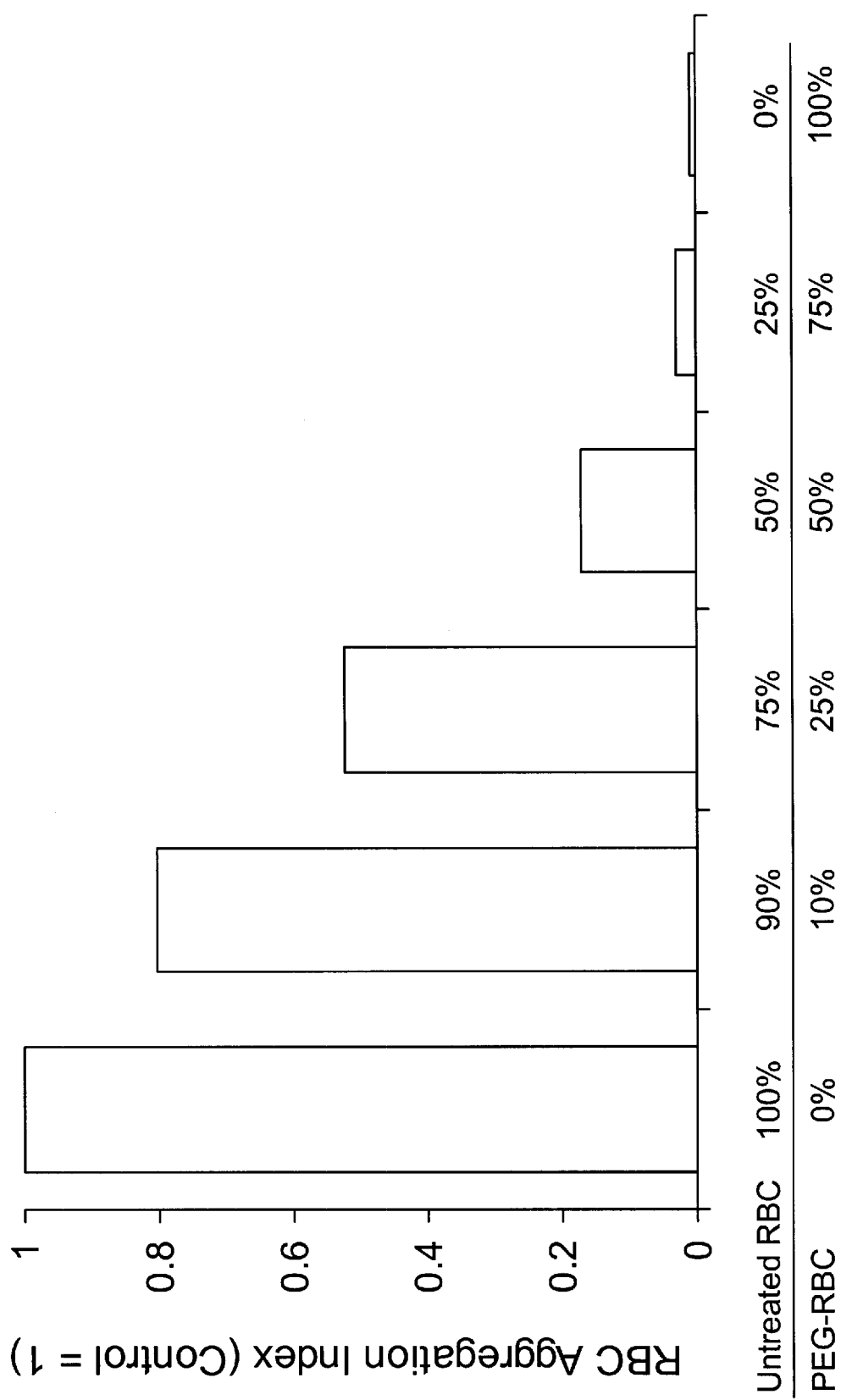
FIG. 7 shows the aggregation of mixtures of untreated and PEG-coated RBC in various proportions at 40% hematocrit measured using the Myrenne aggregometer (n=5). The values are expressed relative to control (100% untreated RBC) and illustrate the proportion of RBCs that are required to be treated to yield a significant rheologic effect.

FIG. 5 shows that PEG-CN 18500 alone was less effective at blocking anti-D binding than PEG-CN 3350 at the same concentration (71% vs. 85%). However, when the PEG-CN 18500 and 3350 were used in combination, an additive effect was observed which resulted in substantial further decrease in anti-D binding (to 96%). This combination of two discrete PEG derivatives having a higher and lower molecular weight ranges respectively has given the best results to date, and typically resulted in a greater degree of masking for antigens other than D, e.g., 97.4% and 99.4% for the Rh antigens c and E, respectively.

The larger molecule, PEG 18500, was more effective at blocking agglutination to the A and I antigens, which are carbohydrates, than were the smaller PEG molecules. These carbohydrate antigens are present in high copy number on the cell, and may be located throughout the glycocalyx at some distance from the nearest adjacent protein.

As the PEG derivatives bind exclusively to proteins, the higher molecular weight PEG, with its larger zone of steric hindrance, is more likely to mask the carbohydrate antigens than the lower molecular weight PEG molecules. In contrast, the flow cytometry results showed that the lower molecular weight PEG 3350 was more effective at masking the Rh antigens. The Rh antigens are located on transmembrane proteins, with their antigenic sites located close to the membrane. Thus, the RBC membrane surface is more accessible to the lower molecular weight PEG molecules, while the higher molecular weight PEG molecules may be excluded by steric interactions with larger RBC surface structures and the RBC glycocalyx.

To achieve the best results, two discrete molecular weight ranges are used. A higher molecular weight range has at least a portion of the range above 10,000 Daltons and a lower range has at least a portion below 10,000. Preferably, the molecular weight range of the lower molecular weight PEG derivative is between approximately 2,000 and 5,000 Daltons, e.g., 3350. The molecular weight range of the higher molecular weight PEG derivative is approximately 10,000–35,000 Daltons and e.g., 18,500. Thus, a preferred RBC formulation according to this invention has RBCs with two species of PEG derivatives having discrete molecular weight ranges covalently bound to the surface: a higher molecular weight species (10,000–35,000 mw). This combination has been demonstrated to yield improved results over either species alone and provides a lower molecular weight species (2,000–5,000 mw) to yield the benefits of a larger hydrodynamic radius (rheological effects) as well as antigen masking.

Using this technique of selecting a plurality of certain PEG derivatives with discrete molecular weight ranges, i.e., with a combination of PEG-CN 18500 and PEG-CN 3500 at 20 mg/ml, between 96 and 99% of anti-D binding can be consistently blocked, with similar or greater inhibition for the other Rh antigens. The use of higher concentrations of these simple linear PEG-CN derivatives can further reduce antibody binding, but was found to severely compromise the RBC morphology. This was especially noticeable with the mPEG-CN 5000 derivative, with which RBC became severely echinocytic at concentrations above 10 mg/ml. Improved PEG derivatives can be created by providing linkers other than dichlorotriazine and by using known polymer molecules with a different geometry to create an even more effective steric barrier while maintaining RBC morphology and deformability.

EXAMPLE 3

Inhibition of RBC Aggregation By PEG Modification of BC

In addition to the antigen masking effects described above, the attachment of PEG also strongly inhibits the aggregation of RBC. The aggregation of RBC in autologous plasma was measured using a Myrenne Aggregometer (Myrenne GmbH, Roetgen, Germany), an instrument which quantifies RBC aggregation by measuring the rate of change of light transmission through a sheared blood sample (R. M. Bauersachs, R. B. Wenby and H. J. Meiselman, Determination of specific red blood cell indices via an automated system, *Clin. Hemorheol*, 9(1989) 1–25). PEG-coated RBC were prepared as described above (control RBC were incubated in buffer alone), after which both PEG-coated and control RBC were resuspended in autologous plasma at 40% hematocrit. Referring to FIG. 6, the effect of incubating RBC with increasing concentrations of mPEG-CN 5000 is shown. RBC aggregation decreased with increasing PEG concentration, and was abolished at a concentration of 5 mg/ml and above. PEG-CN 18500 was more effective, and completely inhibited RBC aggregation at 1 mg/ml (i.e., nearly 20 times more effective on a molar basis).

Furthermore, given that the techniques require ex vivo RBC modification, it would be difficult in practice to treat all of the circulating RBC. The proportion of treated cells required to achieve a significant rheologic effect is shown in FIG. 7. When half of the RBC were treated, aggregation was reduced by >80%, while replacement of just one tenth of RBC with PEG-treated cells reduced aggregation by 20%.

EXAMPLE 4

Poloxamers Bound to the Surface of RBCs

Applying the teachings of this invention, one may select several different polymers for covalent binding to a cell surface. Poloxamers, as described above, are a well-known class of polymers whose efficacy in certain biological situations has been reported. Pursuant to this invention, RBCs may be coated with poloxamers to make an RBC formulation that maintains the antigen masking effects described above while tailoring the viscosity effects as desired by the clinical indication.

TABLE 3

Low Shear Viscosity (0.14985$^{-1}$) at 25° C. and 37° C.

|  | 25° C. | 37° C. |
|---|---|---|
| Control | 57.51 | 44.82 |
| PEG-CN18500 | 13.6 | 9.99 |
| P188-CN | 14.78 | 34.7 |
| P288-CN | 146.3 | 330.69 |

In Table 3 above, difunctional 2,4-dichloro-s-triazine derivatives of poloxamers 188 (mw 8400 Daltons) and F288 (mw 12,000 Daltons) were prepared and incubated at 5 mg/ml with RBCs at 40% hematocrit.

The covalently bound F68 strongly reduces low shear viscosity at 25°. However, at 37° (body temperature), the viscosity is much closer to the control. F188 covalently bound to RBCs is strongly pro-aggregant at both temperatures. Thus, where antigen masking is desired without a low viscosity RBC formulation, the invention provides a selection of polymers that may be utilized.

The particular examples set forth herein are instructional and should not be interpreted as limitations on the applications to which those of ordinary skill are able to apply this invention. Modifications and other uses are available to those skilled in the art which are encompassed within the spirit and scope of the following claims.

We claim:

1. A physiologically compatible solution for infusion comprising;
   red blood cells covalently bound with at least two polyethylene glycol derivatives, wherein a first polyethylene glycol derivative has a molecular weight range of between 2,000 and 5,000 Daltons and wherein a second polyethylene glycol derivative has a molecular weight range of between 10,000 and 35,000 Daltons.

2. The physiologically compatible solution of claim 1 wherein the molecular weight of the second polyethylene glycol derivative is approximately 18,500.

3. The physiologically compatible solution of claim 1 wherein the molecular weight is of the first polyethylene glycol derivative is approximately 3,350.

4. The physiologically compatible solution of claim 1 wherein at least one of the first and second polyethylene glycol derivative is a monofunctional cyanuric chloride derivative.

5. The solution of claim 1 wherein at least one of the first and second polyethylene glycol derivative is a difinctional cyanuric chloride derivative.

6. A method to produce a physiologically compatible solution comprising;
   covalently binding a first polyethylene glycol derivative to a population of red blood cells, wherein the first polyethylene glycol derivative has a molecular weight range of between approximately 2,000–5,000 Daltons, and
   covalently binding a second polyethylene glycol derivative to the red blood cells, wherein the second polyethylene glycol derivative has a molecular weight range of between approximately 10,000–35,000 Daltons.

7. The method of claim 6 wherein the first polyethylene glycol derivative has a molecular weight of approximately 3,350.

8. The method of claim 6 wherein the second polyethylene glycol derivative has a molecular weight of approximately 18,500.

9. The method of claim 6 wherein the first or second polyethylene glycol derivative is a monofinctional cyanuric chloride derivative.

10. The method of claim 6 wherein the first or second polyethylene glycol derivative is a difunctional cyanuric chloride derivative.

* * * * *